United States Patent [19]
Umezawa et al.

[11] 3,965,089
[45] June 22, 1976

[54] PROCESS FOR THE PRODUCTION OF A CYCLIC UREIDO-DERIVATIVE OF A DEOXYSTREPTAMINE-CONTAINING ANTIBIOTIC AND PRODUCTS THEREOF

[75] Inventors: Hamao Umezawa; Kenji Maeda, both of Tokyo; Shinichi Kondo, Yokohama; Shunzo Fukatsu, Tokyo, all of Japan

[73] Assignee: Zaidan Hojin Biseibutsu Kagaku Kenkyu Kai, Tokyo, Japan

[22] Filed: Mar. 12, 1973

[21] Appl. No.: 340,311

[52] U.S. Cl. .................. 260/210 AB; 260/210 K; 260/210 NE; 424/180; 424/181
[51] Int. Cl.² .......................................... C07H 15/22
[58] Field of Search...... 260/210 AB, 210 R, 210 K, 260/210 NE, 211.5 R

[56] References Cited
UNITED STATES PATENTS

| | | | |
|---|---|---|---|
| 2,612,497 | 9/1952 | Meijer | 260/211.5 R |
| 3,769,273 | 10/1973 | Massey | 260/210 AB |
| 3,780,018 | 12/1973 | Konishi et al. | 260/210 AB |
| 3,781,268 | 12/1973 | Kawaguchi et al. | 260/210 AB |

*Primary Examiner*—Johnnie R. Brown
*Attorney, Agent, or Firm*—James C. Haight

[57] ABSTRACT

A new cyclic ureido-derivative of a deoxystreptamine-containing antibiotic represented by the general formula:

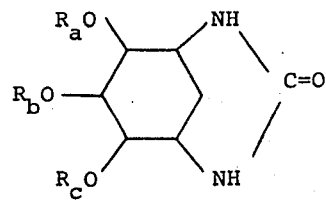

wherein $R_a$, $R_b$ and $R_c$ stand for the residues present in the molecule of said antibiotic other than the deoxystreptamine moiety thereof is produced.

17 Claims, 4 Drawing Figures

PROCESS FOR THE PRODUCTION OF A CYCLIC UREIDO-DERIVATIVE OF A DEOXYSTREPTAMINE-CONTAINING ANTIBIOTIC AND PRODUCTS THEREOF

BACKGROUND OF THE INVENTION

This invention relates to new and useful compounds, namely cyclicureido-derivatives of such aminoglycosidic antibiotics containing a deoxystreptamine moiety in the molecule thereof, for example, kanamycins, neomycins, paromomycins, gentamicins, paromamine ribostamycin and lividomycins. This invention further relates to a process for the production of such new cyclic ureido-derivatives of the antibiotic substances containing a deoxystreptamine moiety in the molecule thereof by converting selectively the two amino groups present in the deoxystreptamine moiety into a cyclic ureido-form.

We have made extensive research to produce a variety of new derivatives from the aminoglycosidic antibiotics containing a deoxystreptamine moiety in the molecule thereof (hereinafter called the deoxystreptamine-containing antibiotics). In our research, we have now found the following fact: a deoxystreptamine-containing antibiotic, that is, the antibiotic containing free two amino groups in the deoxystreptamine moiety thereof as represented by the general formula:

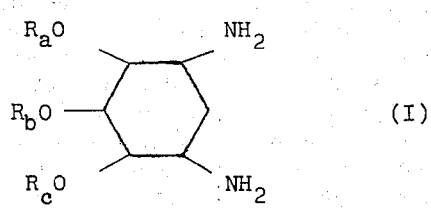

wherein $R_a$, $R_b$ and $R_c$ are each the residues present in the molecule of the deoxystreptamine-containing antibiotic other than the deoxystreptamine moiety of said antibiotic may be reacted with a chloroformate of the formula:

$$Cl-CO-OR_4 \qquad (II)$$

or a p-nitrophenyl carbonic acid ester of the formula:
$$p-NO-C_6H_5-O-CO-OR_4 \qquad (II')$$

or an N-hydroxysuccinimide carbonic acid ester of the formula:

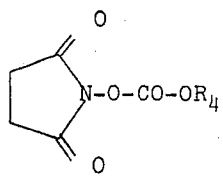

or an azidoformate of the formula:

$$N_3-CO-OR_4 \qquad (II''')$$

wherein $R_4$ stands for an alkyl group, an alkenyl group, a cycloalkyl group, an aralkyl group, an aryl group or a heterocyclic group, to introduce the amino-protecting group $-CO-OR_4$ onto all the amino groups present in the antibiotic of the formula (I), whereby there is prepared a urethane derivative of said antibiotic represented by the general formula:

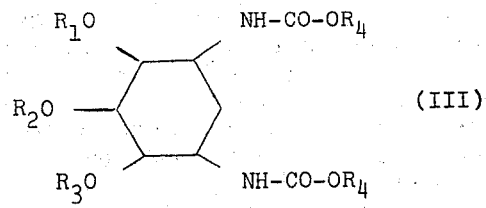

wherein $R_1$, $R_2$ and $R_3$ are such derivative of the groups $R_a$, $R_b$ and $R_c$, respectively, as formed through the reaction of said chloroformate, p-nitrophenyl carbonic acid ester, N-hydroxysuccinimide carbonic acid ester or azidoformate with the aforesaid residues $R_a$, $R_b$ and $R_c$; and $R_4$ has the same meaning as defined above. In case the urethane derivative of the general formula (III) so prepared is subsequently decomposed by reacting with an alkali metal base or an alkaline earth metal base, this urethane derivative (III) may be converted into a cyclic ureido-derivative of the antibiotic represented by the general formula:

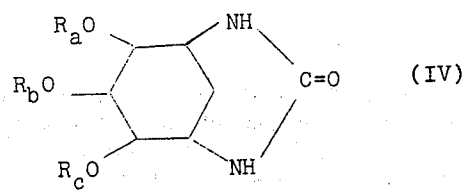

wherein $R_a$, $R_b$ and $R_c$ have the same meanings as defined above and in which the initially free two amino groups of the deoxystreptamine moiety of the antibiotic have been combined together through a carbonyl group in the cyclic ureido-form as shown in the above formula (IV). When this ureido-derivative of the antibiotic of the formula (IV) is then decomposed by reacting with hydrazine, this ureido-derivative can easily undergo a cleavage of the ureido ring with regenerating the free two amino groups. By reacting with hydrazine, therefore, the ureido-derivative of the antibiotic of the formula (IV) can be converted back into the original antibiotic of the formula (I) which contains the free two amino groups in the deoxystreptamine moiety thereof. The cyclic ureido-derivative of the antibiotic of the formula (IV) has its initially free two amino groups of the deoxystreptamine moiety thereof which have been well blocked in the ureido-form, and this cyclic ureido-derivative can readily be transformed or converted into a variety of other derivatives by reacting a variety of reagents with one or more active sites of said cyclic ureido-derivative without bringing about any chemical change in the ureido portion of said ureido-derivative of the antibiotic. Accordingly, the new ureido-derivative of the deoxystreptamine-containing antibiotic of the formula (IV) provides a new route by which a variety of new derivatives of the antibiotic can be produced starting from said antibiotic and by chemically modifying the chemical structure of the antibiotic so as to introduce one or more substituents into one or more reactive sites of the antibiotic. Thus, this new ureido derivative of the deoxystreptamine-containing antibiotic is very useful as intermediate chemical for use in the synthesis of a variety of new derivatives from the antibiotic.

According to a generic, first aspect of the present invention, therefore, there is provided a process for the production of a cyclic ureido-derivative of a deoxystreptamine-containing antibiotic represented by the general formula:

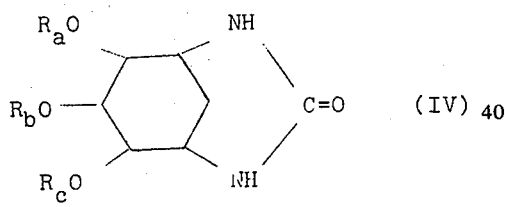

wherein $R_a$, $R_b$ and $R_c$ stand for the residues present in the molecule of said antibiotic other than the deoxystreptamine moiety thereof, which comprises reacting an alkali metal base or an alkaline earth metal base with a urethane derivative of said antibiotic represented by the general formula:

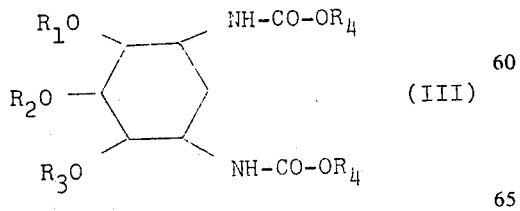

wherein $R_1$ stands for such a derivative of the residue $R_a$ in which all the amino group(s) of said residue $R_a$ has or have been substituted with the amino-protecting group —CO—OR$_4$ as long as the residue $R_a$ initially contains the amino group(s) therein; $R_2$ stands for a derivative of the residue $R_b$ in which all the amino group(s) of said residue $R_a$ has or have been substituted with the amino-protecting group —CO—OR$_4$ as long as the residue $R_b$ initially contains the amino group(s) therein; and $R_3$ stands for such a derivative of the residue $R_c$ in which all the amino group(s) of said residue $R_c$ has or have been substituted with the amino-protecting group —CO—OR$_4$ as long as said residue $R_c$ initially contains the amino group(s) therein; and $R_4$ stands for an alkyl group of 1–5 carbon atoms, an alkenyl group of 2–5 carbon atoms, an aralkyl group, a cycloalkyl group, an aryl group or a heterocyclic group, in which reaction the protected two amino groups present in the deoxystreptamine moiety of said urethane derivative are converted into the cyclic ureido-form as shown in the above formula (IV), simultaneously with that the amino-protecting groups —CO—OR$_4$ attached to the amino-groups present in the aforesaid groups $R_1$, $R_2$ and $R_3$ are liberated from these groups $R_1$, $R_2$ and $R_3$ to regenerate the groups $R_a$, $R_b$ and $R_c$, respectively.

The deoxystreptamine-containing antibiotic from which is derived the urethane derivative of the antibiotic to be used in the process of the present invention may be kanamycin A, kanamycin B, kanamycin C, neamine, neomycin A (neamine), neomycin B, neomycin C, paromamine, paromomycin I, paromomycin II, ribostamycin, lividomycin A, lividomycin B, gentamicin A, gentamicin C and their functional derivatives such as 3',4'-dideoxykanamycin B, tetra-N-alkylkanamycin A, as well as such derivatives of the aforesaid antibiotics in which one or more of the hydroxyl groups present in the molecule thereof has or have been blocked with a known protecting group such as acetyl and benzoyl. In these compounds, $R_a$ is an aminoglycoside and at least one of $R_b$ and $R_c$ is hydrogen.

According to an embodiment of the first aspect of the present invention, therefore, there is provided a process for the production of a cyclic ureido-derivative of a deoxystreptamine-containing antibiotic selected from kanamycin A, kanamycin B, kanamycin C, neamine, neomycin B, neomycin C, paromamine, paromomycin I, paromomycin II, ribostamycin, lividomycin A, lividomycin B, gentamicin A and gentamicin C and represented by the formula:

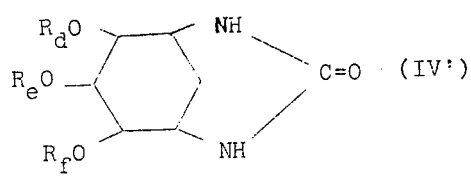

wherein a combination of $R_d$, $R_e$ and $R_f$ is one of the following combinations (i) to (xiv):

i. $R_d$ is 6-amino-6-deoxy-α-D-glucopyranosyl, $R_e$ a hydrogen atom and $R_f$ 3-amino-3-deoxy-α-D-glucopyranosyl (in this case, the compound of the above formula (IV') represents the ureido-derivative of kanamycin A), ii. $R_d$ is 2,6-diamino-2,6-dideoxy-α-D-glucopyranosyl, $R_e$ a hydrogen atom and $R_f$ 3-amino-3-deoxy-α-D-glucopyranosyl (in this case, the compound of the above formula (IV') represents the ureido-derivative of kanamycin B), iii. $R_d$ is α-D-glucosaminyl, $R_e$ a hydrogen atom and $R_f$ 3-amino-3-deoxy-α-D-glucopyranosyl (in this case, the compound of the above formula (IV') represents the ureido-derivative of kanamycin C), iv. $R_d$ is 2,6-diamino-2,6-dideoxy-α-D-glucopyranosyl, $R_e$ a hydrogen atom and $R_f$ a hydrogen atom (in this case, the compound of the above formula (IV') represents the ureido-derivative of neamine), v. $R_d$ is 2,6-diamino-2,6-dideoxy-α-D-glucopyranosyl, $R_e$ 3-O-(2,6-diamino-2,6-dideoxy-α-L-idopyranosyl)β-D-ribofuranosyl and $R_f$ a hydrogen atom (in this case, the compound of the formula (IV') represents the ureido-derivative of neomycin B), vi. $R_d$ is 2,6-diamino-2,6-dideoxy-α-D-glucopyranosyl, $R_e$ 3-O-(2,6-diamino-2,6-dideoxy-α-D-glucopyranosyl)β-D-ribofuranosyl and $R_f$ a hydrogen atom (in this case, the compound of the above formula (IV') represents the ureido-derivative of neomycin C), vii. $R_d$ is α-D-glucosaminyl and $R_e$ and $R_f$ are such a hydrogen atom (in this case, the compound of the above formula (IV') represents the ureido-derivative of paromamine), viii. $R_d$ is α-D-glucosaminyl, $R_e$ 3-O-(2,6-diamino-2,6-dideoxy-α-L-idopyranosyl)β-D-ribofuranosyl and $R_f$ a hydrogen atom (in this case, the compound of the above formula (IV') represents the ureido-derivative of paromomycin I), ix. $R_d$ is α-D-glucosaminyl, $R_e$ 3-O-(2,6-diamino-2,6-dideoxy-α-D-glucopyranosyl)β-D-ribofuranosyl and $R_f$ a hydrogen atom (in this case, the compound of the above formula (IV') represents the ureido-derivative of paromomycin II), x. $R_d$ is 2,6-diamino-2,6-dideoxy-α-D-glucopyranosyl, $R_e$ β-D-ribofuranosyl and $R_f$ a hydrogen atom (in this case, the compound of the above formula (IV') represents the ureido-derivative of ribostamycin), xi. $R_d$ is 2-amino-2,3-dideoxy-α-D-glucopyranosyl, $R_e$ 3-O- 4-O-(α-D-mannòpyranosyl)-2,6-diamino-2,6-dideoxy-α-L-idopyranosyl β-D-ribofuranosyl and $R_f$ a hydrogen atom (in this case, the compound of the above formula (IV') represents the ureido-derivative of lividomycin A), xii. $R_d$ is 2-amino-2,3-dideoxy-α-D-glucopyranosyl, $R_e$ 3-O-(2,6-diamino-2,6-dideoxy-α-L-idopyranosyl)β-D-ribofuranosyl and $R_f$ a hydrogen atom (in this case, the compound of the above formula (IV') represents the ureido-derivative of lividomycin B), xiii. $R_d$ is α-D-glucosaminyl, $R_e$ a hydrogen atom and $R_f$ gentosaminyl (in this case, the compound of the above formula (IV') represents the ureido-derivative of gentamicin A), and xiv. $R_d$ is purpurosaminyl, $R_e$ a hydrogen atom and $R_f$ garosaminyl (in this case, the compound of the above formula (IV') represents the ureido-derivative of gentamicin C), which process comprises reacting a chloroformate of the formula:

$$Cl-CO-OR_4 \quad (II)$$

or a p-nitrophenyl carbonic acid ester of the formula:

$$p-NO_2-C_6H_5-O-CO-OR_4 \quad (II')$$

or a N-hydroxysuccinimide carbonic acid ester of the formula:

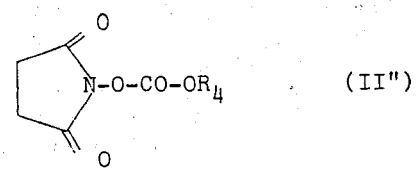

(II'')

or a azidoformate of the formula:

$$N_3-CO-OR_4 \quad (II''')$$

wherein $R_4$ stands for an alkyl group of 1–5 carbon atoms, an alkenyl group of 2–5 carbon atoms, a cycloalkyl group, an aralkyl group, an aryl group or a heterocylic group, with one antibiotic selected from kanamycin A, kanamycin B, kanamycin C, neamine, neomycin B, neomycin C, paromamine, paromomycin I, paromomycin II, ribostamycin, lividomycin A, lividomycin B, gentamicin A and gentamicin C to introduce the amino-protecting group —CO—OR$_4$ onto all the amino groups present in the starting antibiotic employed and thereby to prepare the urethane derivative of said antibiotic in which all the amino groups have been blocked with the amino-protecting group —CO—OR$_4$, and then reacting an alkali metal base or an alkaline earth metal base with said urethane derivative of the antibiotic prepared, whereupon the protected two amino groups present in the deoxystreptamine moiety of said urethane derivative are converted into the cyclic ureido-form, simultaneously with that the amino-protecting groups —CO—OR$_4$ attached to the amino groups present in the other moieties than the deoxystreptamine moiety of said urethane derivative are liberated therefrom.

According to a limited embodiment of the first aspect of the present invention, there is further provided a process for the production of a cyclic ureido-derivative of a deoxystreptamine-containing antibiotic selected from kanamycin A, kanamycin B, kanamycin C, neamine, paromamine and ribostamycin A, which comprises reacting ethyl chloroformate with the antibiotic to introduce the ethoxycarbonyl groups onto all the amino groups of the starting antibiotic employed and thereby to prepare the fully N-ethoxycarbonylated derivative of said antibiotic, and then reacting barium hydroxide with the resulting N-ethoxycarbonyl derivative of the antibiotic in a reaction medium consisting essentially of a mixture of ethylene glycol and water.

In the process according to the present invention, principally the deoxystreptamine-containing antibiotic employed as the initial starting material is firstly reacted with a chloroformate of the formula Cl—CO—OR$_4$ or a p-nitrophenyl carbonic acid ester of the formula p-NO$_2$—C$_6$H$_5$—O—CO—OR$_4$ or an N-hydroxysuccinimide carbonic acid ester of the formula

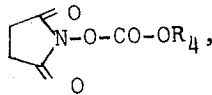

or an azidoformate of the formula N$_3$—CO—OR$_4$, so that all the amino groups present in the molecule of the antibiotic are protected by the introduction thereonto of the known amino-protecting group —CO—OR$_4$ which is derived from the chloroformate, p-nitrophenylcarbonic acid ester, N-hydroxysuccinimide carbonic acid ester or azidoformate employed. In this way, the urethane derivative of the antibiotic (III) is prepared, in which all the amino groups present in the antibiotic molecule have been converted into the urethane form —NH—CO—OR$_4$. This urethane derivative of the antibiotic is then treated by reacting with an alkali metal base or alkaline earth metal base, so that the two amino groups which are initially present in the free form in the deoxystreptamine moiety of the starting antibiotic and which are now protected with the amino-protecting group —CO—OR$_4$ in the urethane derivative of the antibiotic are cyclised into the ureido-form. Upon this reaction of the urethane derivative with the alkali metal or alkaline earth metal base, at the same time, the amino-protecting groups —CO—OR$_4$ which have been attached to the amino groups present in the other positions than in the deoxystreptamine portion of the molecule of the urethane derivative are removed from the amino groups to which they have been attached, to regenerate the free amino groups. The quantity of the chloroformate, p-nitrophenyl carbonic acid ester, N-hydroxysuccinimide carbonic acid ester or azidoformate employed may be 1 mol. or a slight excess per one amino group of the amino groups present in 1 mol. of the deoxystreptamine-containing antibiotic employed with which the chloroformate, p-nitrophenyl carbonic acid ester, N-hydroxysuccinimide carbonic acid ester or azidoformate is to be reacted. The quantity of the alkali metal or alkaline earth metal base employed to be reacted with the urethane derivative of the antibiotic may be such that it makes alkaline the reaction mixture containing said urethane derivative.

In the chloroformate of the formula Cl—CO—OR$_4$, the p-nitrophenyl carbonic acid ester of the formula p-NO$_2$—C$_6$H$_5$—O—CO—OR$_4$ the N-hydroxysuccinimide carbonic acid ester of the formula

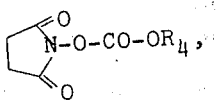

or a azidoformate of the formula N$_3$—CO—OR$_4$ which is used to convert the initial antibiotic into its urethane derivative, the group R$_4$ may be an alkyl group of 1–5 carbon atoms such as methyl, ethyl, t-butyl, t-amyl; an alkenyl group of 2–5 carbon atoms such as allyl; a cycloalkyl group such as cyclopentyl; an aralkyl group such as benzyl and p-nitro-benzyl; an aryl group such as phenyl; and a heterocyclic group such as furfuryl. In carrying out the reaction of the chloroformate, p-nitrophenyl carbonate, N-hydroxysuccinimide carbonate or azidoformate with the initial antibiotic to introduce the amino-protecting group —CO—OR$_4$ into said antibiotic and thus to convert said antibiotic into its urethane derivative, this reaction may be performed in a manner known in the prior art of peptide synthesis. For instance, the reaction of ethyl chloroformate with the initial antibiotic may be carried out by dissolving or suspending the chloroformate and the antibiotic together in an appropriate solvent such as water, ethyl alcohol, acetone or a mixture thereof and effecting the reaction under neutral or alkaline conditions. The ethoxycarbonyl group derived from the ethyl chloroformate is then attached to the free amino groups of the initial antibiotic employed, yielding the urethane derivative, namely the N-ethoxycarbonyl derivative of the antibiotic.

In carrying out the reaction of an alkali metal or alkaline earth metal base with the aforesaid urethane derivative, this reaction may conveniently be performed by dissolving or suspending the base and the urethane derivative together in an appropriate solvent in which both the base and urethane derivative are soluble or dispersible, such as water, methanol, ethanol, ethylene glycol, dioxane, dimethyl formamide or a mixture thereof. The alkali metal base or alkaline earth metal base which is used for this reaction may be sodium hydroxide, barium hydroxide, sodium methylate, sodium ethylate and the like. The reaction temperature may vary depending on the nature of the reactants, the nature of the solvent employed and the reaction time. For instance, the reaction may be effected by heating a solution of the urethane derivative and sodium hydroxide in a mixture of ethylene glycol and water or in methanol for 16–20 hours under reflux, so that the urethane derivative is decomposed to give the ureido-derivative of the antibiotic. In general, the conversion of the urethane derivative into the ureido-derivative of the antibiotic may be effected to completion by heating the reaction mixture for 3–20 hours under reflux. This decomposition reaction of the antibiotic urethane derivative with the metal base may preferably be performed using the urethane derivative containing the ethoxycarbonyl groups as the amino-protecting group and by reacting barium hydroxide therewith in a solvent system consisting essentially of a mixture of water and ethylene glycol, because in this case the conversion of the urethane derivative into the ureido-derivative of the antibiotic takes place in a substantially quantitative yield.

To isolate the ureido-derivative of the antibiotic of the general formula (IV) or (IV') from the reaction mixture, this reaction mixture may at first be neutralised by addition of a mineral acid such as hydrochloric acid or sulfuric acid, and the neutralised reaction mixture may then be passed through a column of a cation-exchange resin such as a cation-exchange resin made of a copolymer of methacrylic acid with divinylbenzene (e.g. commercially available under a registered trade name "Amberlite IRC 50") in the form of ammonium salt to render the ureido-derivative of the antibiotic adsorbed on the resin. The resin column containing the ureido-derivative adsorbed therein is then washed with water and subsequently eluted with aqueous ammonia, while the concentration of ammonia in the eluting solution is gradually increased. The fractions of the eluate containing the ureido-derivative of the antibiotic are collected.

The cyclic ureido-derivative of the deoxy-streptamine-containing antibiotic represented by the above-mentioned general formula (IV), and particularly the ureido-derivatives of kanamycin A, kanamycin B, kanamycin C, neamine, neomycin B, neomycin C, paromamine, paromomycin I, paromomycin II, ribostamycin, lividomycin A, lividomycin B, gentamicin A and gentamicin C represented by the formula (IV') are all new compounds and are useful as intermediate substances from which the production of further new derivatives of the antibiotics may be expected. According to the second aspect of the present invention, therefore, there is provided a cyclic ureido-derivative of a deoxystreptamine-containing antibiotic represented by the general formula:

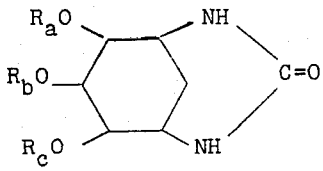

(IV)

wherein $R_a$, $R_b$ and $R_c$ stand for the residues present in the molecule of the aforesaid antibiotic other than the deoxystreptamine moiety thereof.

According to an embodiment of the second aspect of the present invention, there is provided a cyclic ureido-derivative of a deoxystreptamine-containing antibiotic selected from kanamycin A, kanamycin B, kanamycin C, neamine, neomycin B, neomycin C, paromamine, paromomycin I, paromomycin II, ribostamycin, lividomycin A, lividomycin B, gentamicin A and gentamicin C and represented by the formula:

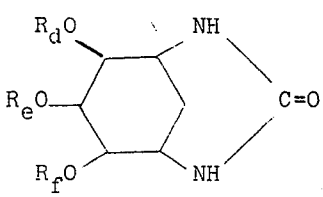

(IV')

wherein a combination of $R_d$, $R_e$ and $R_f$ is one of the following combinations (i) to (xiv):

i. $R_3$ is 6-amino-6-deoxy-α-D-glucopyranosyl, $R_e$ a hydrogen atom and $R_f$ 3-amino-3-deoxy-α-D-glucopyranosyl, ii. $R_d$ is 2,6-diamino-2,6-dideoxy-α-D-glucopyranosyl, $R_e$ a hydrogen atom and $R_f$ 3-amino-3-deoxy-α-D-glucopyranosyl, iii. $R_d$ is a α-D-glucosaminyl, $R_e$ a hydrogen atom and $R_f$ 3-amino-3-deoxy-α-D-glucopyranosyl, iv. $R_d$ is 2,6-diamino-2,6-dideoxy-α-D-glucopyranosyl, $R_e$ a hydrogen atom and $R_f$ a hydrogen atom.

v. $R_d$ is 2,6-diamino-2,6-dideoxy-α-D-glucopyranosyl, $R_e$ 3-O-(2,6-diamino-2,6-dideoxy-α-L-idopyranosyl)-β-D-ribofuranosyl and $R_f$ a hydrogen atom, vi. $R_d$ is 2,6-diamino-2,6-dideoxy-α-D-glucopyranosyl, $R_e$ 3-O-(2,6-diamino-2,6-dideoxy-α-D-glucopyranosyl)-β-D-ribofuranosyl and $R_f$ a hydrogen atom, vii. $R_d$ is α-D-glucosaminyl and $R_e$ and $R_f$ are each a hydrogen atom, viii. $R_d$ is α-D-glucosaminyl, $R_e$ 3-O-(2,6-diamino-2,6-dideoxy-α-L-idopyranosyl)-β-D-ribofuranosyl and $R_f$ a hydrogen atom, ix. $R_d$ is α-D-glucosaminyl, $R_e$ 3-O-(2,6-diamino-2,6-dideoxy-α-D-glucopyranosyl)-β-D-ribofuranosyl and $R_f$ a hydrogen atom, x. $R_d$ is 2,6-diamino-2,6-dideoxy-α-D-glucopyranosyl, $R_e$ β-D-ribofuranosyl and $R_f$ a hydrogen atom, xi. $R_d$ is 2-amino-2,3-dideoxy-α-D-glucopyranosyl, $R_e$ 3-O-[4-O-(α-D-mannopyranosyl)-2,6-diamino-2,6-dideoxy-α-L-idopyranosyl]-β-D-ribofuranosyl and $R_f$ a hydrogen atom, xii. $R_d$ is 2-amino-2,3-dideoxy-α-D-glucopyranosyl, $R_e$ 3-O-(2,6-diamino-2,6-dideoxy-β-L-idopyranosyl)-β-D-ribofuranosyl and $R_f$ a hydrogen atom, xiii. $R_d$ is α-D-glucosaminyl, $R_e$ a hydrogen atom and $R_f$ gentosaminyl, and xiv. $R_d$ is purpurosaminyl, $R_e$ a hydrogen atom and $R_f$ garosaminyl.

According to a more limited embodiment of the second aspect of the present invention, there is provided a cyclic ureido-derivative of a deoxy-streptamine-containing antibiotic selected from kanamycin A, kanamycin B, kanamycin C, neamine, paromamine and ribostamycin A.

Referring to the attached drawings.

Figure 1:
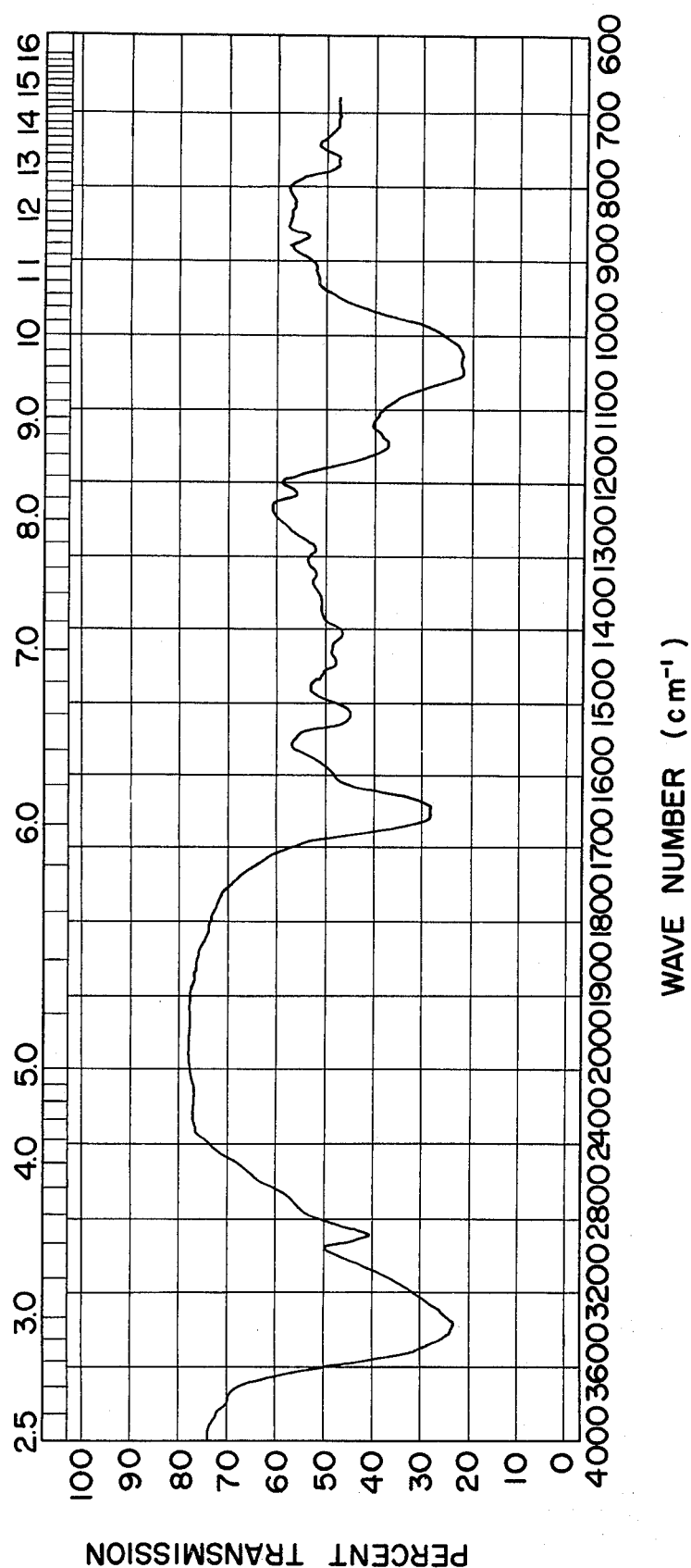
FIG. 1 shows a curve of infrared absorption spectrum of the cyclic ureido-derivative of kanamycin A according to the present invention pelleted in potassium bromide.
Figure 2:
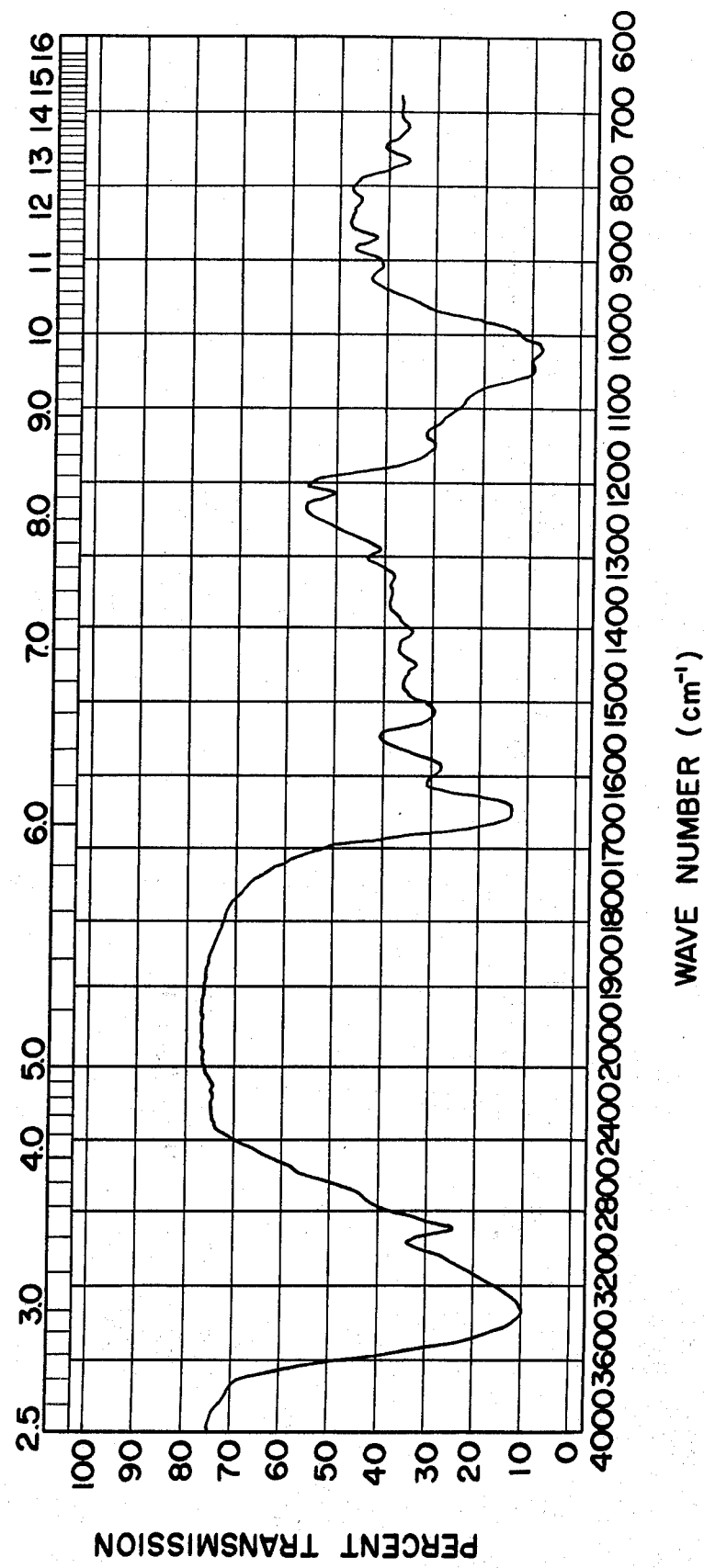
FIG. 2 shows a curve of infrared absorption spectrum of the cyclic ureido-derivative of kanamycin B according to the present invention pelleted in potassium bromide.
Figure 3:
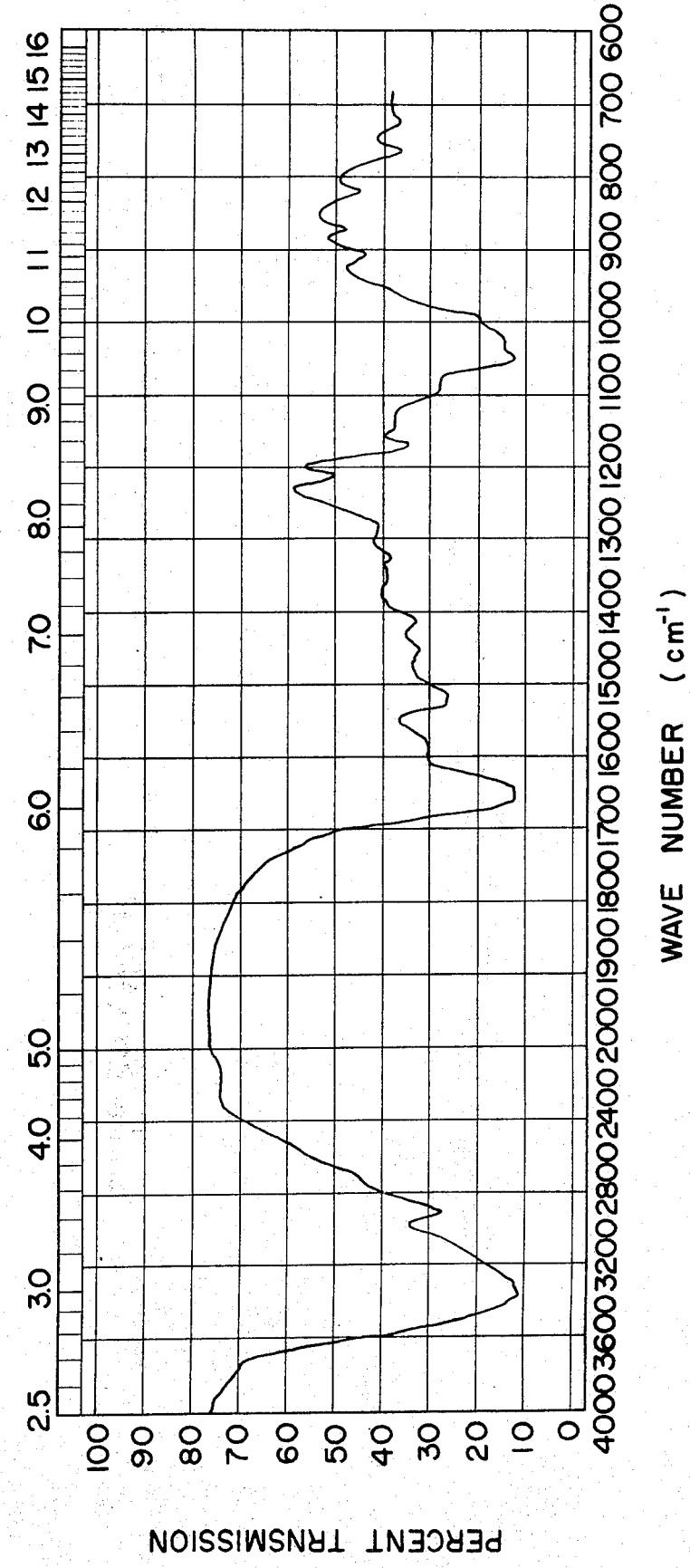
FIG. 3 shows a curve of infrared absorption spectrum of the cyclic ureido-derivative of neomycin A according to the present invention pelleted in potassium bromide.
Figure 4:
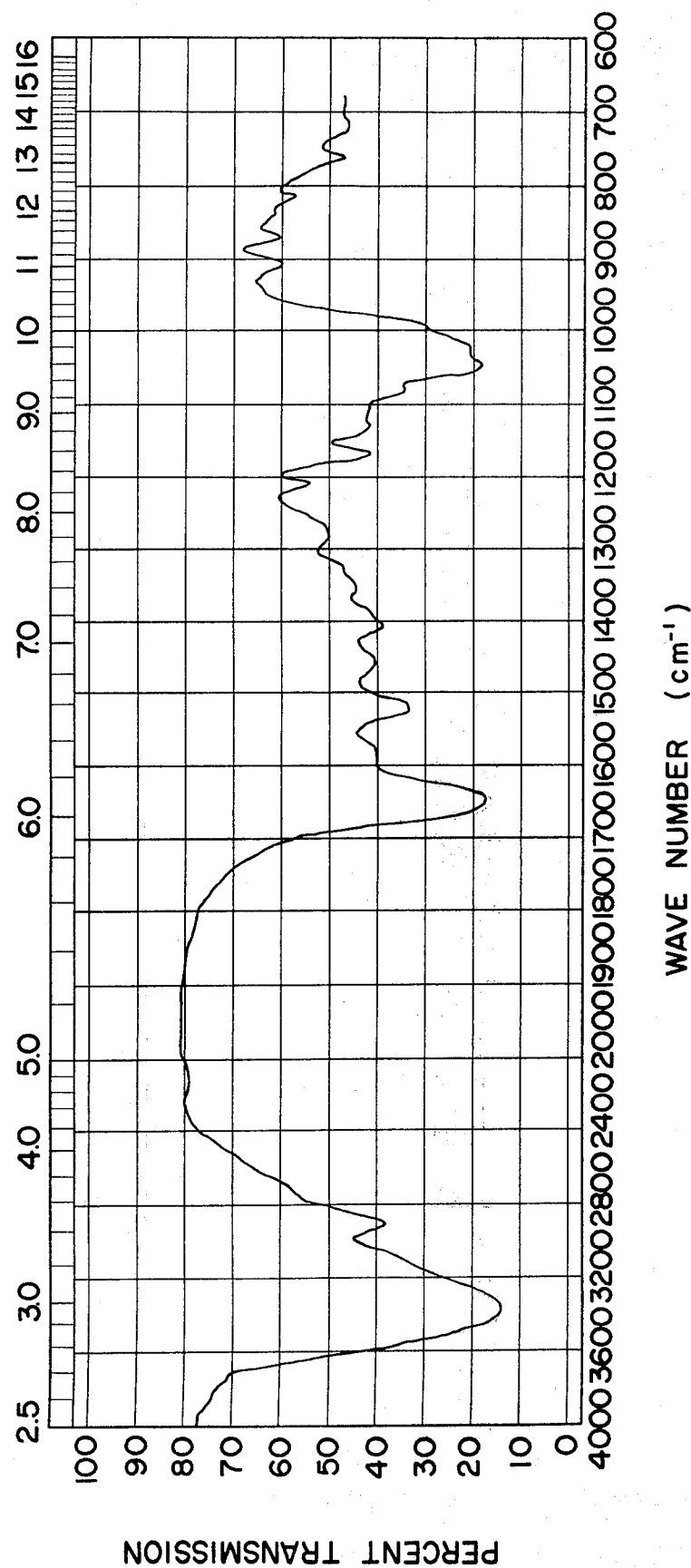
FIG. 4 shows a curve of infrared absorption spectrum of the cyclic ureido-derivative of paromamine according to the present invention pelleted in potassium bromide.

The decomposition reaction of the ureido-derivative of the antibiotic with hydrazine may be carried out efficiently, for example, by heating a mixture of the ureido-derivative and hydrazine hydrate placed in a sealed tube at 130°C for 48 hours, or by heating the ureido-derivative together with hydrazine hydrate in methyl cellosolve for 24 hours under reflux, or by heating the ureido-derivative together with anhydrous hydrazine in methyl cellosolve for 24 hours under reflux.

The present invention is now illustrated with reference to the following Examples but to which the present invention is not limited.

EXAMPLE 1

20 g (34 milli-mole) of a kanamycin A sulfate (potency 750 mcg/mg) was substantially dissolved in a mixture of 90 ml. of water and 90 ml. of acetone to which 10 g. of anhydrous sodium carbonate was then added. To the resulting mixture was added dropwise 16.2 g. (149 milli-mole) of ethyl chloroformate under ice-cooling. The mixture was agitated for 1.5 hours at room temperature while it was maintained at a pH of 8 or above by occasional addition of an aqueous 50% sodium hydroxide. A white precipitate deposited, and this was removed by filtration, washed with water and dried to give 23.8 g. (31 milli-mole) of the tetra-N-ethoxy-carbonyl kanamycin A in a yield of 90%.

To this tetra-N-ethoxycarbonyl kanamycin A were added 230 ml. of methanol and 36.8 g. of sodium hydroxide, and the resulting mixture was heated for 16 hours under reflux over an oil bath at 80C. The reaction mixture was then diluted with an equal volume of water and then neutralised by addition of 6N hydrochloric acid. The neutralised reaction mixture was then passed through a column of 540 ml. of a cation-exchange resin made of a copolymer of methacrylic acid with divinylbenzene (which is commercially available under a registered trade name "Amberlite CG 50" produced by Rohm & Haas, U.S.A.) in the form of ammonium salt, to make the reaction products adsorbed in the resin of the column. The column was then washed with water and then eluted with a 0.1 N aqueous ammonia. The eluate was collected in fractions each of a 54 ml. volume. The fractions No. 25 to 28 were taken and combined together, and the combined solution was concentrated under a reduced pressure and freeze-dried to give 4.5 g. of the cyclic ureido-derivative of kanamycin A in the form of a white powder in a yield of 25%. This ureido-derivative of kanamycin A showed a decomposition point of 238°C. $[\alpha]_D^{21} = +146°$ (c 1, water).

Elemental analysis.
Found: C, 42.81%; H, 7.18%, N, 10.63%; O, 39.59%.
Calculated for $C_{19}H_{34}N_4O_{12} \cdot H_2O$: C, 43.18%; H, 6.87%; N, 10.60%; O, 39.36%.

By the N.M.R. spectrum, infrared absorption spectrum and chemical analysis, it was confirmed that the cyclic ureido-derivative of kanamycin A produced in this Example had the following structure:

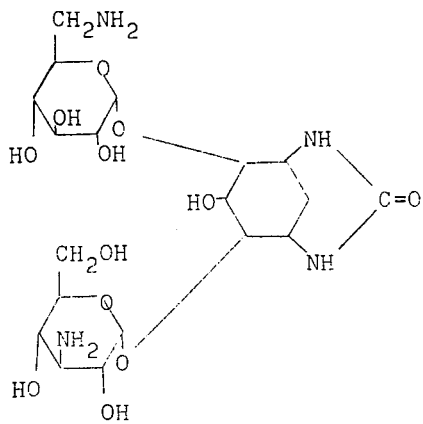

EXAMPLE 2

Kanamycin B was reacted with ethyl chloroformate in the same manner as in Example 1 to give the penta-N-ethoxycarbonyl kanamycin B. 4.0 g. (4.7 milli-mole) of the penta-N-ethoxycarbonyl kanamydin B was dissolved in 34.6 ml. of methanol containing 4.4 g. of sodium hydroxide. The solution was heated for 16 hours under reflux in an oil bath at 80°C, and the reaction mixture was then added with an equal volume of water and neutralised by addition of 6N hydrochloric acid. This neutralised reaction mixture was passed through a column of 100 ml. of a cation-exchange resin made of a copolymer of methacrylic acid with divinylbenzene in the form of the ammonium salt (commercially available under a registered trade name "Amberlilte CG 50") to make the antibiotic derivative adsorbed by the resin. The recovery and purification of the cyclic ureido-derivative of kanamycin B so produced was then effected chromatographically in the same manner as in Example 1 by eluting the resin column with aqueous ammonia. 1.4 g of the ureido-derivative of kanamycin B was obtained in the form of a white powder in a yield of 55%. Recrystallisation from water gave a more purified cyclic ureido-derivative of kanamycin B in the form having needles of a decomposition point of 197°C. $[\alpha]_D^{21} = +160°$ (c 1, water).

Elemental analysis.
Found: C, 41.52%; H, 7.18%; N,13.11%; O, 38.38%.
Calculated for $C_{19}H_{35}N_5O_{11} \cdot 2H_2O$: C, 41.83%; H, 7.21%; N, 12.84%; O, 38.13%.

By the N.M.R. spectrum, infrared absorption spectrum and chemical analysis, it was confirmed that the ureido-derivative of kanamycin B produced in this Example had the following structure:

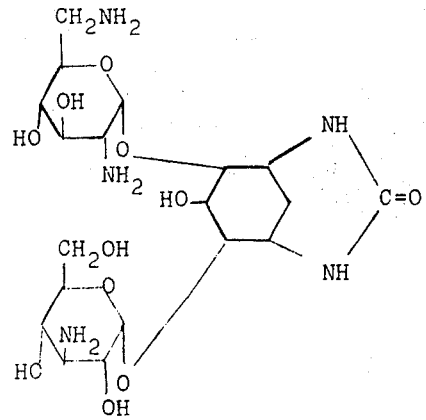

EXAMPLE 3

15 g (17.8 milli-mole) of the penta-N-ethoxycarbonyl kanamycin B prepared in Example 2 was suspended in 400 ml. of a 3:1 mixture of ethylene glycol and water to which 33 g of barium hydroxide octahydrate was then added. The mixture was heated for 20 hours under reflux in an oil bath at 160°C, and the reaction mixture was then added with a three-fold volume of water. A precipitate deposited, which was removed by filtration and the filtrate was neutralised by passing gaseous carbon dioxide thereinto to precipitate barium carbonate. After the barium carbonate was filtered off, the solution was passed through a column of 200 ml. of a cation-exchange resin made of a copolymer of methacrylic acid with divinylbenzene in the form of the ammonium salt (commercially available under a registered trade name "Amberlite CG 50") to effect the adsorption of the cyclic ureido-derivative of kanamycin B by the resin. The recovery and purification of this ureido-derivative was made chromatographically in the same manner as in Example 1 by eluting with aqueous ammonia. The cyclic ureido-derivative of kanamycin B was obtained in the form of a white crystalline powder and in a yield of 6.5 g (67%).

EXAMPLE 4

Neamine was reacted with ethyl chloroformate in the same manner as in Example 1 to give the tetra-N-ethoxycarbonyl neamine. (22 g. (36 milli-mole) of the tetra-N-ethoxycarbonyl neamine so prepared was suspended in 90 ml. of methanol containing 24.2 g of sodium hydroxide. The mixture was heated for 16 hours under reflux in an oil bath at 80°C. The reaction mixture was diluted by addition of an equal volume of water and then neutralised by addition of 6N hydrochloric acid. The neutralised reaction mixture was passed through a column of 440 ml. of a cation-exchange resin made of a copolymer of methacrylic acid with divinylbenzene in the form of the ammonium salt (commercially available under a registered trade name "Amberlite IRC 50", a product of Rohm & Haas Co., U.S.A.), to effect the adsorption of the cyclic ureido-derivative of neamine by the resin. The recovery and purification of the ureido-derivative was made chromatographically in the same manner as in Example 1 by eluting the resin column with aqueous ammonia. The ureido-derivative of neamine was obtained in the form of a white crystalline powder of a decomposition point of 176°C and in a yield of 5.1 g (39%). $[\alpha]_D^{21} = +155°$ (c 1, water).

Elemental analysis.
Found: C, 42.08%; H, 7.47%; N, 15.35%; O, 34.66%.
Calculated for $C_{13}H_{24}N_4O_7 \cdot H_2O$: C, 42.62%; H, 7.15%; N, 15.29%; O, 34.94%.

By the N.M.R. spectrum, infrared absorption spectrum and chemical analysis, it was confirmed that the cyclic ureido-derivative of neamine produced in this Example had the following structure:

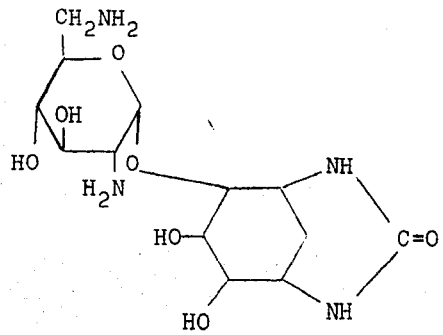

EXAMPLE 5

Paramamine was reacted with ethyl chloroformate in the same manner as in Example 1 to give the tri-N-ethoxycarbonyl paromamine. 344 mg (0.64 milli-mole) of the tri-N-ethoxycarbonyl paromamine so prepared was mixed with 3.4 ml. of water, 10.3 ml. of ethylene glycol and 757 mg. of barium hydroxide. The resulting suspension was heated for 16 hours under reflux in an oil bath at 160°C. The reaction mixture was then diluted by addition of 30 ml. of water and then neutralised by addition of hydrochloric acid. The neutralised reaction mixture was chromatographically treated in the same manner as in Example 1 to recover and purify the cyclic rueido-derivative of paromamine. This product was obtained in the form of a white crystalline powder with a decomposition point of 206°C and in a yield of 184 mg. (83%). $[\alpha]_D^{21} = +132°$ (c 1, water).

Found: C, 42.31%; H, 7.01%; N, 11.39%; O, 38.98%.
Calculated for $C_{13}H_{23}N_3O_8 \cdot H_2O$: C, 42.50%; H, 6.86%; N, 11.44%; O, 39.20%.

By the N.M.R. spectrum, infrared absorption spectrum and chemical analysis, it was confirmed that the cyclic ureido-derivative of paromamine produced in this Example had the following structure:

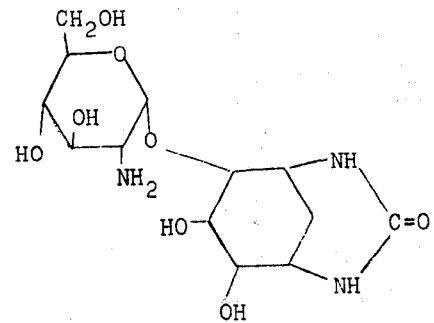

EXAMPLE 6

Ribostamycin was reacted with ethyl chloroformate in the same manner as in Example 1 to give the tetra-N-ethoxycarbonyl ribostamycin. 22 g (29.6 milli-mole) of the tetra-N-ethoxycarbonyl ribostamycin so prepared was suspended in 190 ml. of methanol containing 24.2 g of sodium hydroxide. The mixture was heated for 16 hours under reflux in an oil bath at 80°C. The reaction mixture was diluted by addition of an equal volume of water and then neutralised by addition of 6N hydrochloric acid. The neutralised reaction mixture was chromatographed on cation exchange resin (440 ml.) in the same manner as in Example 4 to give the ureido-derivative of ribostamycin in the form of a white crystalline powder (4.8 g, 34%), m.p. 166°C (decomp.), $[\alpha]_D^{18} = +56°$ (c 1, water).

By the N.M.R. spectrum, infrared absorption spectrum and chemical analysis, it was confirmed that the cyclic ureido-derivative of ribostamycin produced in this Example had the following structure:

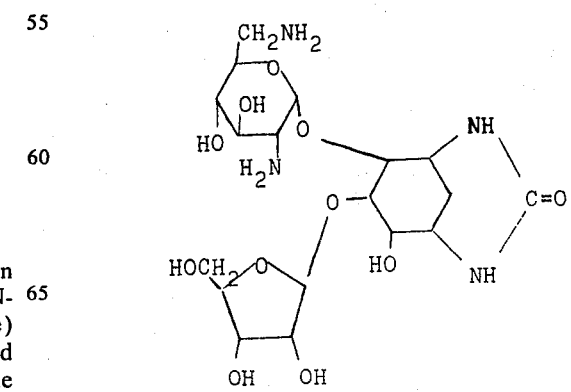

EXAMPLE 7

101 mg. of the cyclic ureido-derivative of kanamycin B obtained in Example 3 was dissolved in 2 ml. of hydrzine hydrate, and the solution was heated at 130°C for 48 hours in a sealed glass tube. The reaction mixture was concentrated to dryness by evaporation of hydrazine under a reduced pressure. The solid residue was dissolved in 10 ml. of water and the aqueous solution was passed through a column of 20 ml. of a cation-exchange resin made of a copolymer of methacrylic acid with divinylbenzene (commercially available under a registered trade name "Amberlite CG 50", a product of Rohn & Haas Co., U.S.A.) in the form or the ammonium salt to effect the adsorption of the cyclic ureido-derivative by the resin. The column was washed with water and then eluted with 0.3N aqueous ammonia. The elutate was collected in fractions, and those fractions exhibiting an antibacterial activity to *Bacillus subtilis* were taken and combined together. The combined solution was concentrated to dryness by evaporation under a reduced pressure to give 70 mg. of a white powder. Yield 73%. This powder was identified as kanamycin B by comparing its physical, chemical and biological properties with those of a known sample of kanamycin B.

What we claim is:

1. The cyclic ureido-derivative of a deoxystreptamine-containing antibiotic of the formula:

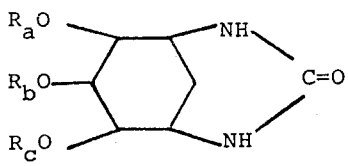

wherein $R_a$ is an aminoglycoside present in the molecule other than on the deoxystreptamine moiety thereof, $R_b$ and $R_c$ are each hydrogen or an aminoglycoside present in the molecule of the antibiotic other than on the deoxystreptamine moiety thereof.

2. A compound according to claim 1, wherein one of $R_b$ and $R_c$ is an aminoglycoside.

3. A compound according to claim 1, wherein $R_b$ and $R_c$ are both hydrogen.

4. A compound according to claim 1, wherein said antibiotic is selected from the group consisting of kanamycin A, kanamycin B, kanamycin C, neamine, neomycin B, neomycin C, paromamine, paromomycin I, paromomycin II, ribostamycin, lividomycin A, lividomycin B, gentamicin A and gentamicin C.

5. A compound according to claim 4, wherein said antibiotic is selected from the group consisting of kanamycin A, kanamycin B, kanamycin C, neamime, paromamine and ribostamycin.

6. The cyclic ureido-derivative of kanamycin A represented by the formula:

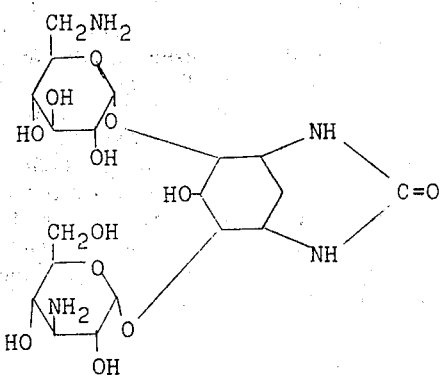

7. The cyclic ureido-derivative of kanamycin B represented by the formula:

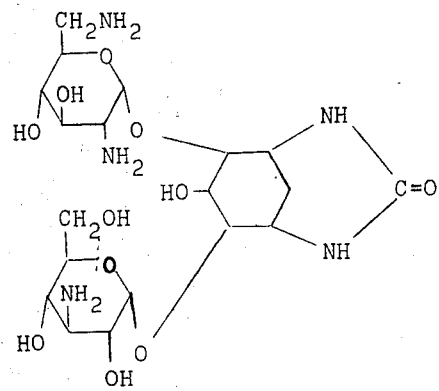

8. The cyclic ureido-derivative of neamine represented by the formula:

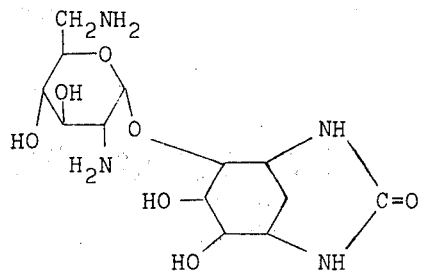

9. The cyclic ureido-derivative of paromamine represented by the formula:

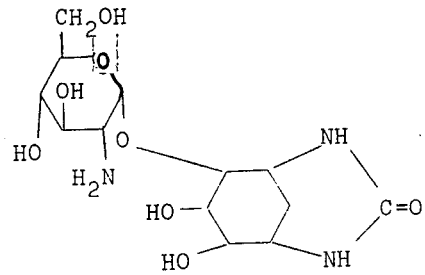

10. The cyclic ureido-derivative of ribostamycin represented by the formula:

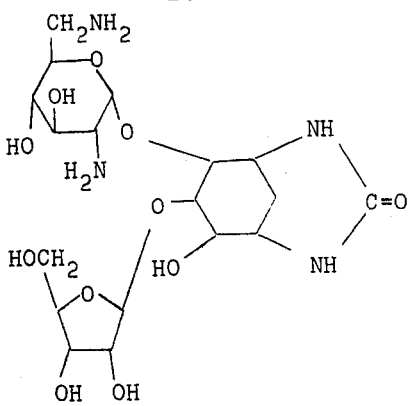

11. A process for the production of cyclic ureido-deoxystreptamine-containing antibiotics of the formula:

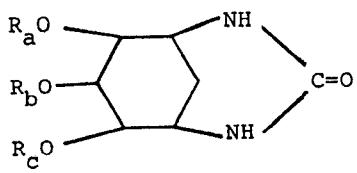

wherein $R_a$ is an aminoglycoside present in the molecule of the antibiotic other than on the deoxystreptamine moiety thereof and $R_b$ and $R_c$ are each hydrogen or an aminoglycoside present in the molecule of said antibiotic other than on the deoxystreptamine moiety thereof, which comprises reacting in an inert solvent: (a) an alkali metal base or an alkaline earth metal base in an amount sufficient to provide an alkaline reaction mixture, with (b) a urethane derivative of said antibiotic of the formula:

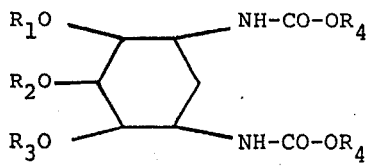

wherein $R_1$, $R_2$ and $R_3$ are each amino-protected derivatives of $R_a$, $R_b$ and and $R_c$, respectively in which all of the aminoglycoside groups originally present therein are substituted with an amino-protecting group of the formula $-CO-OR_4$ wherein $R_4$ is alkyl of 1–5 carbon atoms, alkenyl of 2–5 carbon atoms, aralkyl, cycloalkyl, aryl or a monovalent heterocyclic group, to:

i. convert the two protected amino groups $-NH-CO-OR_4$ in the deoxystreptamine moiety of said urethane derivative into the cyclic ureido form, and simultaneously ii. liberate said amino-protecting groups from $R_1$, $R_2$ and $R_3$ whereby the aminoglycoside members of $R_a$, $R_b$ and $R_c$ are regenerated.

12. A process according to claim 11, wherein the deoxstreptamine-containing antibiotic is selected from the group consisting of cyclic ureido derivatives of kanamycin A, kanamycin B, kanamycin C, neamine, neomycin B, neomycin C, paromamine, paromomycin I, paromomycin II, ribostamycin, lividomycin A, lividomycin B, gentamicin A and gentamicin C.

13. A process according to claim 12, wherein the deoxystreptamine-containing antibiotic is selected from the group consisting of kanamycin A, kanamycin B, kanamycin C, neamine, paromamine and ribostamycin.

14. A process according to claim 11, wherein $R_4$ is alkyl of 1–5 carbon atoms, alkenyl of 2-5 carbon atoms, cyclopentyl, phenyl, benzyl, p-nitrobenzyl or furfuryl.

15. A process according to claim 13, wherein said base is barium hydroxide.

16. A process according to claim 11, in which the deoxystreptamine-containing antibiotic is selected from the group consisting of cyclic ureido derivatives of kanamycin A, kanamycin B, kanamycin C, neamine, neomycin B, neomycin C, paromamine, paromomycin I, paromomycin II, ribostamycin, lividomycin A, lividomycin B, gentamicin A and gentamicin C, further comprising preparing said urethane derivative by reacting said antibiotic with a member selected from the group consisting of a chloroformate of the formula $Cl-CO-OR_4$, a nitrophenyl carbonic acid ester of the formula $p-NO_2-C_6H_5-O-CO-R_4$, an N-hydroxysuccinimide carbonic acid ester of the formula:

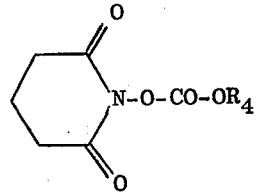 and an azidoformate of the formula $N_3-CO-OR_4$ wherein $R_4$ has the above-indicated values.

17. A process according to claim 16, wherein said urethane derivatives are prepared in a reaction mixture containing an acid binding agent.

* * * * *